(12) United States Patent
Hendriks et al.

(10) Patent No.: US 10,531,921 B2
(45) Date of Patent: Jan. 14, 2020

(54) TISSUE SEALING DEVICE WITH OPTICAL FEEDBACK

(71) Applicant: KONINKLIJKE PHILIPS N.V., Eindhoven (NL)

(72) Inventors: Bernardus Hendrikus Wilhelmus Hendriks, Eindhoven (NL); Torre Michelle Bydlon, Eindhoven (NL); Vishnu Vardhan Pully, Eindhoven (NL); Charles Frederik Sio, Eindhoven (NL); Sandra Martina Van Den Bosch, Eindhoven (NL); Gerhardus Wilhelmus Lucassen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 385 days.

(21) Appl. No.: 15/327,165

(22) PCT Filed: Jul. 14, 2015

(86) PCT No.: PCT/EP2015/066026
§ 371 (c)(1),
(2) Date: Jan. 18, 2017

(87) PCT Pub. No.: WO2016/012302
PCT Pub. Date: Jan. 28, 2016

(65) Prior Publication Data
US 2017/0156797 A1    Jun. 8, 2017

(30) Foreign Application Priority Data

Jul. 22, 2014 (EP) .................................... 14178017
Nov. 14, 2014 (EP) .................................... 14193278

(51) Int. Cl.
*A61B 18/04*    (2006.01)
*A61B 18/22*    (2006.01)
(Continued)

(52) U.S. Cl.
CPC ............ *A61B 18/22* (2013.01); *A61B 5/0075* (2013.01); *A61B 5/0084* (2013.01); *A61B 18/04* (2013.01);
(Continued)

(58) Field of Classification Search
CPC ... A61B 18/04; A61B 18/1442; A61B 18/203; A61B 18/22; A61B 18/24;
(Continued)

(56) References Cited

U.S. PATENT DOCUMENTS 5,762,609 A * 6/1998 Benaron .............. A61B 5/0084
600/473
5,769,791 A    6/1998 Benaron
(Continued)

FOREIGN PATENT DOCUMENTS

EP    2529687 A2    12/2012
EP    2742892 A1    6/2014
(Continued)

OTHER PUBLICATIONS

Lee, B.H. et al, "Fiber-based optical coherence tomography for biomedical imaging, sensing, and precision measurements", Optical Fiber Technology 2013, vol. 19, pp. 729-740.
(Continued)

*Primary Examiner* — Michael F Peffley

(57) ABSTRACT

The present invention relates to a method for determining a state of tissue sealing during a tissue sealing process. According to the disclosed method, an optical probe beam is used to irradiate a tissue region. A signal indicative of optical scattering in the tissue region is generated from a portion of the optical probe beam that has passed through or been returned by the tissue region. The onset of tissue sealing is indicated by the successive occurrence in time of a turning point and a point of inflection in the optical scattering signal.

(Continued)

An energy-based tissue sealing or tissue-cutting device for use in accordance with the method is also disclosed.

20 Claims, 4 Drawing Sheets

(51) Int. Cl.
| | |
|---|---|
| *A61B 5/00* | (2006.01) |
| *A61B 18/20* | (2006.01) |
| *A61B 18/24* | (2006.01) |
| *A61B 18/00* | (2006.01) |
| *A61B 17/00* | (2006.01) |
| *A61B 18/14* | (2006.01) |

(52) U.S. Cl.
CPC .......... *A61B 18/203* (2013.01); *A61B 18/24* (2013.01); *A61B 2017/00061* (2013.01); *A61B 2018/0063* (2013.01); *A61B 2018/00642* (2013.01); *A61B 2018/00678* (2013.01); *A61B 2018/1455* (2013.01); *A61B 2018/2261* (2013.01)

(58) Field of Classification Search
CPC ........... A61B 2017/00057; A61B 2017/00061; A61B 2018/0063; A61B 2018/00642; A61B 2018/00678; A61B 2018/00702; A61B 2018/1455; A61B 2018/2261; A61B 5/0075; A61B 5/0084
See application file for complete search history.

(56) References Cited

U.S. PATENT DOCUMENTS

| | | | |
|---|---|---|---|
| 6,228,076 B1 | 5/2001 | Winston | |
| 6,594,518 B1* | 7/2003 | Benaron | A61B 5/0059 600/342 |
| 8,777,945 B2 | 7/2014 | Floume et al. | |
| 9,763,642 B2 | 9/2017 | Harks et al. | |
| 2010/0217258 A1* | 8/2010 | Floume | A61B 5/0059 606/34 |
| 2012/0010603 A1 | 1/2012 | Milner | |
| 2012/0296238 A1* | 11/2012 | Chernov | A61B 18/1442 601/2 |
| 2013/0253489 A1 | 9/2013 | Nau et al. | |
| 2013/0289591 A1 | 10/2013 | Boudreaux et al. | |
| 2014/0171806 A1* | 6/2014 | Govari | A61B 5/0086 600/476 |
| 2015/0289767 A1 | 10/2015 | Keller | |

FOREIGN PATENT DOCUMENTS

| | | |
|---|---|---|
| JP | H09117456 A | 5/1997 |
| JP | 2003135482 A | 5/2003 |
| WO | 2009005850 A1 | 1/2009 |
| WO | 2009153719 A1 | 12/2009 |
| WO | 2013108194 A2 | 7/2013 |

OTHER PUBLICATIONS

Song, C. et al, "Fiber-optic OCT sensor guided SMART microforceps for microsurgery," Biomedical Optics Express, Jul. 2013, vol. 4(7), pp. 1045-1050.

Goncharov, A.F., "Raman Spectroscopy at High Pressures", International Journal of Spectroscopy, 2011, vol. 2012, Article ID 617528,16 pages.

Ewinger, A. et al, "In situ measurement of the temperature of water in microchannels using laser Raman spectroscopy", Chemical Engineering Journal, 2013, vol. 223, pp. 129-134.

Floume, Timmy et al "Optical, Thermal, and Electrical Monitoring of Radio-Frequency Tissue Modification", Journal of Biomedical Optics, vol. 15, No. 1, Feb. 2010, pp. 018003.

Latka, Ines et al, "Fiber optic probes for linear and nonlinear Raman applications Current trends and future development," Laser Photonics Rev. 2013, vol. 7(5), pp. 698-731.

Tjin, G. et al, "Quantification of collagen I in airway tissues using second harmonic generation," Journal of Biomedical Optics , 2014, vol. 19(3), pp. 036005 (1-10).

Zhang, Y. et al "A compact fiber-optic SHG scanning endomicroscope and its application to visualize cervical remodeling during pregnancy", PNAS Early Edition, 2012, pp. 1-6.

Helmchen, F. "Dynamic Confocal Imaging of Living Brain, Miniaturization of fluorescence microscopes using fiber optics," Experimental Physiology: Translation and Integration , (2002) 87.6, pp. 737-745.

Wu, J. et al, "Automated quantification and reconstruction of collagen matrix from 3D confocal datasets" J. Microsc., 2002, vol. 210, pp. 158-165.

Engelbrecht, C. J. et al, "Ultra-compact fiber-optic two-photon microscope for functional fluorescence imaging in vivo," Optics Express, vol. 16 (8), Apr. 14, 2008, pp. 5556-5564.

Agarwal, A. et al., "Two-Photon Laser Scanning Microscopy of Epithelial Cell-Modulated Collagen Density in Engineered Human Lung Tissue," Tissue Engineering, vol. 7(2), 2001, pp. 191-202.

Müller, M. et al, "Recovering intrinsic fluorescence by Monte Carlo modeling", J. Biomed. Optics vol. 18 (2013) p. 027009-1 to 027009-13.

Nachabe, Rami et al "Estimation of lipid and water concentrations in scattering media with diffuse optical spectroscopy from 900 to 1600 nm," Journal of Biomedical Optics, vol. 15, May 2010, pp. 037015-10.

Nachabe, Rami et al, "Estimation of biological chromophores using diffuse optical spectroscopy : benefit of extending the UV-VIS wavelength range to include 1000 to 1600 nm," Optics Express, vol. 18, 2010, pp. 879-888.

Ferrell, Thomas J. et al, "A diffusion theory model of spatially resolved, steady-state diffuse reflectance for the non-invasive determination of tissue optical properties," Med. Phys. 19 (1992) p. 879-888.

Nachabe, Rami et al "Effect of bile absorption coefficents on the estimation of liver tissue optical properties and related implications in discriminating healthy and tumorous samples", Optical Society of America, 2011.

* cited by examiner

TISSUE SEALING DEVICE WITH OPTICAL FEEDBACK

CROSS-REFERENCE TO PRIOR APPLICATIONS

This application is the U.S. National Phase application under 35 U.S.C. § 371 of International Application No. PCT/EP2015.066026, filed on Jul. 14, 2015, which claims the benefit of European Patent Application No. 14178017.1, filed on Jul. 22, 2014 and European Patent Application No. 14193278.0, filed on Nov. 14, 2014. These applications are hereby incorporated by reference herein.

FIELD OF THE INVENTION

The invention relates to a method for indicating a state of tissue sealing and finds application in the surgical field. The method may be used in conjunction with an energy-based tissue-sealing or tissue cutting device.

BACKGROUND OF THE INVENTION

In surgery, energy-based tissue sealing devices are used in procedures such as laparoscopy to haemostatically seal blood vessels and arteries. Such devices, otherwise known as tissue-bonding, or tissue-welding devices apply heat to a tissue region in order to induce tissue transformations such as the denaturation of proteins, the dehydration of tissue, and to alter collagen bonds. Energy is typically delivered to the tissue region in the form of Radio Frequency (RF) or High Frequency RF by electrodes that contact the tissue, for example in a clamping device such as the Ligasure™ marketed by the Covidien corporation. Other devices envisage to deliver energy to tissue regions in the form of optical or thermal energy. Tissue sealing may also occur to some extent on the remaining tissue following an intervention with an energy-based tissue cutting device.

Since tissue composition can vary significantly between different patients and in different parts of the body, adaptation of the tissue sealing or tissue cutting device settings is typically necessary during the sealing or cutting process respectively in order to obtain the best possible seal. At present the thermal and electrical impedance of the tissue are used as feedback signals to control the RF settings of the device. However, these parameters typically provide only partial information about the tissue, which limits the benefits offered by such feedback.

U.S. Pat. No. 5,762,609 relates to the use of optical feedback in such surgical tools, wherein it is disclosed to determine a tissue state dynamically during surgical interventions in a tissue welding device. U.S. Pat. No. 5,762,609 discloses to measure optical transmittance at specific wavelengths, and to measure optical parameters such as absorbance, scattering, anisotropy factor, elastic scattering, polarisation and fluorescence. The determination of specific tissue states is suggested as being possible using such data through empirical analysis and techniques such as class analysis and partial components regression.

In order to address the drawbacks of the above techniques and systems, the present invention seeks to improve the reliability of a tissue seal formed during a tissue sealing or tissue cutting process.

SUMMARY OF THE INVENTION

It is an object of the invention to provide an improved method for the identification of tissue states such as the onset of tissue sealing, and the termination of tissue sealing. This may be used during a tissue sealing process in order to confirm the integrity of a tissue seal, and further to control the sealing power or energy of a tissue sealing or tissue cutting device used in such procedures. A further object of the invention is to provide a device for use in conjunction with the method.

In accordance with one aspect of the invention a method is disclosed for determining a state of tissue sealing. The method comprises the steps of: irradiating a tissue region with an optical probe beam; receiving at least a portion of the optical probe beam that has passed through or been returned by the tissue region; generating a signal indicative of optical scattering in the tissue region from the received optical probe beam; indicating an onset of tissue sealing based on the successive occurrence in time of a turning point and a point of inflection in the optical scattering signal. The method may be used to more accurately indicate the onset of tissue sealing. The tissue region may alternatively be the tissue sealing zone of an energy-based tissue-sealing or tissue cutting device.

In accordance with another aspect of the invention the onset of tissue sealing is indicated based further on a second turning point in the optical scattering signal, wherein the second turning point in the optical scattering signal succeeds the point of inflection. The monitoring of the second turning point improves the reliability of the indication of the onset of tissue sealing.

In accordance with another aspect of the invention the onset of tissue sealing is indicated based further on a second point of inflection in the optical scattering signal, wherein the second point of inflection in the optical scattering signal succeeds the second turning point. The monitoring of the second point of inflection improves the reliability of the indication of the onset of tissue sealing.

In accordance with another aspect of the invention the method further comprises the step of indicating a termination of tissue sealing. The termination of tissue sealing is indicated based on a third turning point in the optical scattering signal, wherein the third turning point in the optical scattering signal succeeds the second turning point. The determination of the termination of tissue sealing is important in identifying when to reduce or turn off the power of a tissue sealing device in order to prevent charring of tissue.

In accordance with another aspect of the invention the method further comprises the step of generating a signal indicative of water content in the tissue region from the received optical probe beam; wherein the onset of tissue sealing is indicated based further on a reduction of water content in the tissue immediately prior to the turning point. The monitoring of water content in this way may be used to confirm the onset of tissue sealing.

In accordance with another aspect of the invention the method further comprises the step of generating a signal indicative of at least one of: water, collagen, lipid, elastin, β-carotene, lycopene, α-carotene, oxyhaemoglobin, de-oxyhaemoglobin, methaemoglobin, or exogenous dye content in the tissue region from the received optical probe beam; wherein either the onset of tissue sealing, or the termination of tissue sealing is indicated based further on at least one of said parameters traversing a predetermined threshold. The generation of such additional signals may be used to further improve the accuracy of determination of a state of tissue sealing.

In accordance with another aspect of the invention a computer program product having instruction for carrying out the various method aspects of the invention is disclosed. The computer program product may be a computer-readable data-carrier such as a CD, a DVD, a disk-drive, a memory card, a ROM, a RAM, or a downloadable file stored on a server.

In accordance with other aspects of the invention, methods of controlling a tissue sealing power of a thermal or optical tissue sealing device in accordance with the above tissue states, and various tissue sealing or tissue cutting devices employing such are disclosed.

DETAILED DESCRIPTION OF THE INVENTION

In order to improve the determination of tissue states during a tissue sealing process, the present invention is described in relation to a forceps, or clamp-type tissue sealing device in which RF energy is used to seal the tissue. It is however to be appreciated that the invention also finds application in the identification of a tissue sealing state in tissue sealing devices having other forms of energy delivery and other forms of tissue-retention during sealing. The invention also finds application in tissue cutting devices such as an electro-surgical knife. In such devices the cutting of tissue by the knife may act to seal the remaining tissue; consequently the invention may be used to monitor the integrity of the resulting seal and to provide feedback to the cutting process to optimise the seal. The method of the invention also finds application in surgical probes in general; for example in the determination of a tissue sealing state after a tissue-sealing process has been carried out.

The present invention arises from an insight into specific changes that occur to tissue composition during an energy-based tissue-sealing process. By monitoring optical parameters indicative of these changes a more accurate determination of the state of tissue sealing may be provided.

Figure 1:
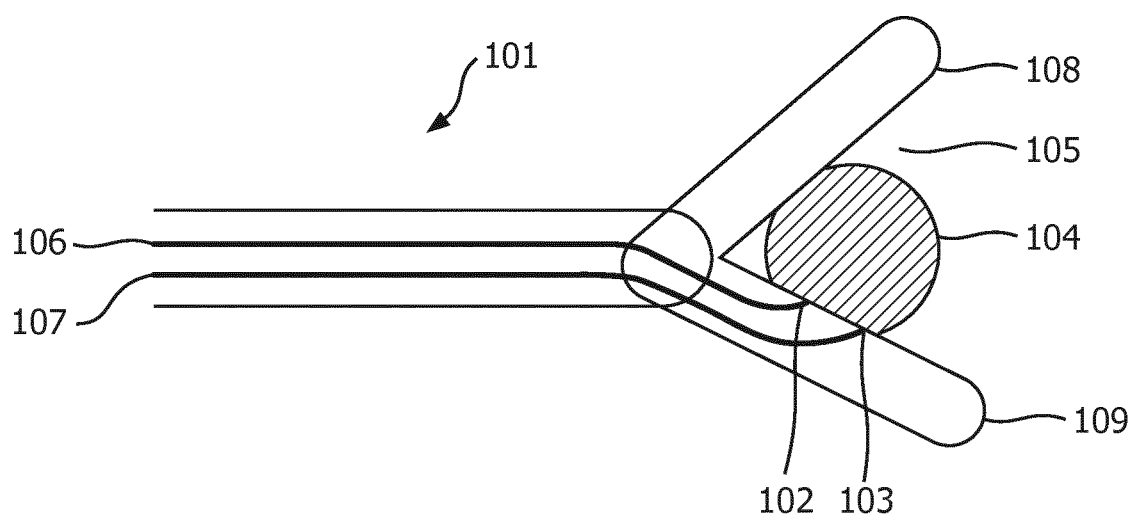
FIG. 1 schematically illustrates a clamp-type tissue sealing tool 101 having optical fibers embedded in its clamp jaws.

FIG. 1 schematically illustrates a clamp-type tissue sealing tool 101 having optical fibers embedded in its clamp jaws. The tissue sealing tool of FIG. 1 was used to generate experimental optical data corresponding to different states of tissue sealing. In FIG. 1, two optical fibers 102, 103 are shown. Source optical fiber 102 is used to irradiate exemplary tissue region 104, such as a portion of a human or animal body, with an optical probe beam; and detector optical fiber 103 receives some of the optical probe beam that has been returned by the tissue region 104 within tissue sealing region 105 of the sealing tool 101. In this configuration optical reflection and scattering cause some of the optical probe beam delivered by the source optical fiber 102 to be returned to detector optical fiber 103; the remaining portion of the optical probe beam being transmitted through or absorbed within tissue region 104, thus within tissue sealing region 105. Optical fibers 102, 103 are in communication at their distal ends 106, 107 respectively with an optical source, not shown, and a spectrophotometer, not shown. A broadband halogen optical source generating optical wavelengths from the visible wavelength range to the infrared was used, the source having significant emission in the range 400 nm to 1700 nm. Such a configuration is generally termed a diffuse reflectance setup. During operation the spectrophotometer measures the spectrum of the optical probe beam that has been returned by tissue 104 within tissue sealing region 105. During tissue sealing, clamp jaws 108, 109 of the tissue sealing tool 101 are closed onto exemplary tissue region 104 whilst RF power is applied to electrodes embedded within clamp jaws 108, 109 in order to deliver energy to the tissue region in order to heat and ultimately to seal the tissue. Consequently optical spectra of the probe beam that has been returned by tissue sealing region 105 may be acquired over time during the tissue sealing process. These spectra are typically dominated by optical reflection and scattering effects.

The device illustrated in FIG. 1 was used to investigate changes in the diffuse reflectance spectra that occurred over time during a tissue sealing process carried out on an exemplary section of swine intestine. Optical parameters were subsequently extracted from the spectra using an algorithm, the development of which the inventors have previously contributed to. The algorithm can be used to derive optical tissue properties such as the scattering coefficient and absorption coefficient of different tissue chromophores: e.g. deoxygenated haemoglobin, oxygenated haemoglobin, methaemoglobin, bile, β-carotene, α-carotene, lycopene, water, lipid, collagen, elastin, and exogenous dyes from the reflectance spectra. These properties may change during the course of the tissue sealing procedure, and also differ between different tissue types. Based on this knowledge it is possible to discriminate between various tissue sealing states, different kinds of tissue and/or discriminate between various conditions of a tissue. The present inventors have developed this algorithm such that a sufficiently certain and real-time optical analysis can be performed in context of performing electro-surgery with an electro-surgical system as described in the present application.

In order to extract the desired optical parameters, the acquired spectra may be fitted using a custom made Matlab 7.9.0 (Mathworks, Natick, Mass.) algorithm. In this algorithm, a widely accepted analytical model was implemented, namely the model introduced by the reference by T. J. Farrel, M. S. Patterson and B. C. Wilson, "A diffusion theory model of spatially resolved, steady-state diffuse reflectance for the non-invasive determination of tissue optical properties", Med. Phys. 19 (1992) p. 879-888, which is hereby incorporated by reference in entirety. The input arguments for the model of this reference are the absorption coefficient $\mu_a(\lambda)$, the reduced scattering coefficient $\mu_s'(\lambda)$ and the center-to-center distance between the emitting and collecting fibers at the tip of the probe.

In the following part, the model will be explained briefly. The used formulas are mainly based on work of Nachabé et al., and reference is thus made to R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442, which is hereby incorporated by reference in entirety, and furthermore reference is made to R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010), which is also hereby incorporated by reference in entirety.

A double power law function can be used to describe the wavelength dependence of the reduced scattering, where the wavelength $\lambda$ is expressed in nm and is normalized to a wavelength value of $\lambda_0=800$ nm. The parameter $\alpha$ corresponds to the reduced scattering amplitude at this specific wavelength.

$$\mu_s(\lambda) = \alpha \left( \rho_{MR} \left(\frac{\lambda}{\lambda_0}\right)^{-b} + (1-\rho_{MR})\left(\frac{\lambda}{\lambda_0}\right)^{-4} \right) [\text{cm}^{-1}] \quad (\text{Eq. 1})$$

In this equation the reduced scattering coefficient is expressed as the sum of Mie and Rayleigh scattering where $\rho_{MR}$ is the Mie-to-total reduced scattering fraction. The reduced scattering slope of the Mie scattering is denoted b and is related to the particle size. For a homogeneous distribution of absorbers, the total light absorption coefficient $\mu_a(\lambda)$ can be computed as products of the extinction coefficients and volume fraction of the absorbers (see FIG. 2)

$$\mu_\alpha^{Total} = f_1\mu_\alpha^1 + f_2\mu_\alpha^2 + f_3\mu_\alpha^3 + \ldots \quad (\text{Eq. 2})$$

This total absorption $\mu_\alpha^{Total}$ can be written as $$\mu_\alpha^{Total} = \mu_\alpha^{Tissue}(\lambda) + f_{other}\mu_\alpha^{other} \quad (\text{Eq. 3})$$

where $\mu_a^{Tissue}(\lambda)$ is the absorption due to blood, water and lipid and where $\mu_a^{other}(\lambda)$ correspond to the remaining chromophores such as beta-carotene, methaemoglobin, bile, collagen, elastin.

Instead of modeling the absorption coefficient $\mu_a^{Tissue}(\lambda)$ as the sum of absorption coefficients weighted by the respective concentrations of the four chromophores of interest, it was decided to express the tissue absorption coefficient for blood, water and lipid as $$\mu_\alpha^{Tissue}(\lambda) = C(\lambda)v_{Blood}\mu_\alpha^{Blood}(\lambda) + v_{WL}\mu_\alpha^{WL}(\lambda) \ [\text{cm}^{-1}] \quad (\text{Eq. 3a})$$

where $\mu_a^{Blood}(\lambda)$ corresponds to the absorption by blood and $\mu_a^{WL}(\lambda)$ corresponds to absorption by water and lipid together in the probed volume. The volume fraction of water and lipid is $v_{wL}=[\text{Lipid}]+[\text{H}_2\text{O}]$, whereas $v_{Blood}$ represents the blood volume fraction for a concentration of haemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as $$C(\lambda) = \frac{1 - \exp(-2R\mu_a^{Blood}(\lambda))}{2R\mu_a^{Blood}(\lambda)} \quad (\text{Eq. 4})$$

where R denotes the average vessel radius expressed in cm. The absorption coefficient related to blood is given by $$\mu_\alpha^{Blood}(\lambda) = \alpha_{BL}\mu_\alpha^{HbO2}(\lambda) + (1-\alpha_{BL})\mu_\alpha^{Hb}(\lambda) \ [\text{cm}^{-1}] \quad (\text{Eq. 5})$$

where $\mu_a^{HbO2}(\lambda)$ and $\mu_a^{Hb}(\lambda)$ represent the basic extinction coefficient spectra of oxygenated haemoglobin HbO$_2$ and deoxygenated haemoglobin Hb, respectively. The oxygenated haemoglobin fraction in the total amount of haemoglobin is noted $\alpha_{BL}=[\text{HbO}_2]/([\text{HbO}_2]+[\text{Hb}])$ and is commonly known as the blood oxygen saturation. The absorption due to the presence of water and lipid in the measured tissue is defined as $$\mu_\alpha^{WL}(\lambda) = \alpha_{WL}\mu_\alpha^{Lipid}(\lambda) + (1-\alpha_{WL})\mu_\alpha^{H2O}(\lambda)[\text{cm}^{-1}] \quad (\text{Eq. 6})$$

In this case the concentration of lipid related to the total concentration of lipid and water together can be written as $\alpha_{WF}=[\text{Lipid}]/([\text{Lipid}]+[\text{H}_2\text{O}])$, where [Lipid] and [H$_2$O] correspond to the concentration of lipid (density of 0.86 g/ml) and water, respectively.

This way of relating the water and lipid parameters in the expression of the absorption coefficient defined in Eq. 6, rather than estimating separately the water and lipid volume fraction corresponds to a minimization of the covariance of the basic functions for fitting resulting in a more stable fit cf. the reference R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442. For further explanation and validation of this theorem reference is made to the reference R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

For example by means of the described algorithm optical tissue properties may be derived such as the scattering coefficient and absorption coefficient of different tissue chromophores: e.g. haemoglobin, oxygenated haemoglobin, water, fat etc. For further explanation see also R. Nachabé, D. J. Evers, B. H. W. Hendriks G. W. Lucassen, M. van der Voort, J. Wesseling and T. J. M. Ruers, "Effect of bile absorption coefficient on the estimation of liver tissue optical properties and related implications in discriminating healthy and tumorous samples" Bomedical Optcis express 2, pp 600-614 (2011).

Figure 2:
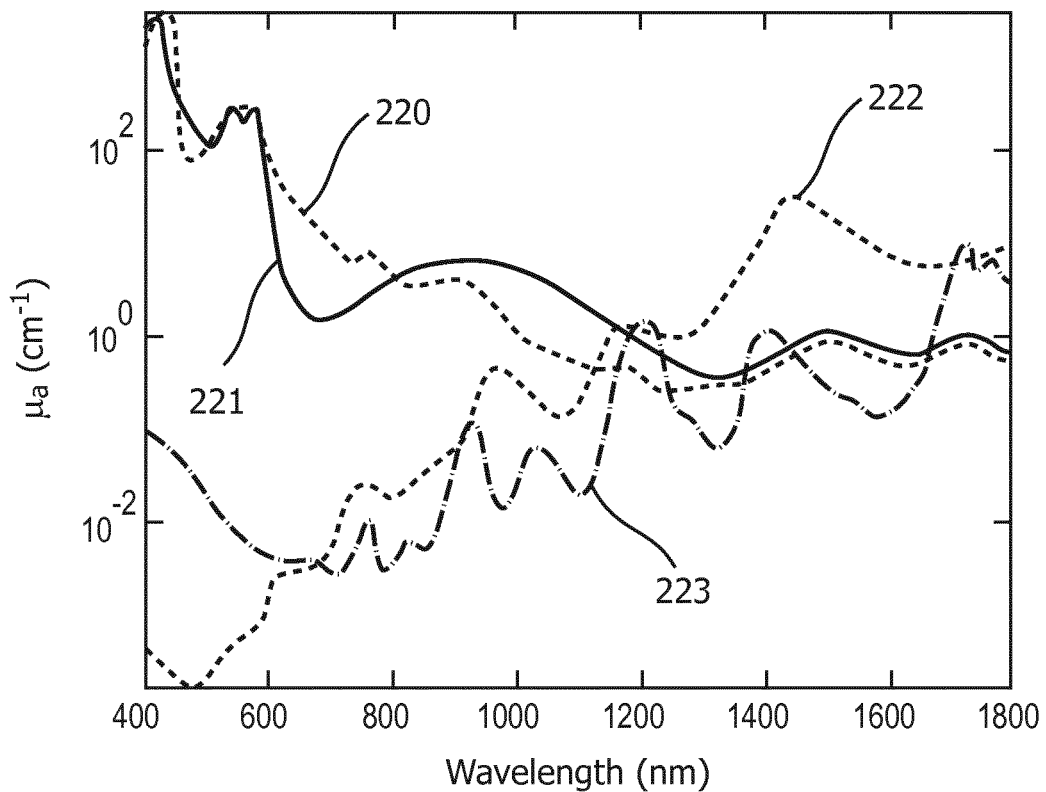
FIG. 2 illustrates optical absorption spectra in the visible and near-infrared range of some of the most important chromophores present in the human body, specifically blood, water and lipid.

FIG. 2 illustrates optical absorption spectra in the visible and near-infrared range of some of the most important chromophores present in the human body, specifically blood, water and lipid. The graph shows absorption coefficients of deoxygenated haemoglobin (Hb) 220, oxygenated haemoglobin (HbO$_2$) 221, water 222 and lipid 223 as a function of the wavelength. Note that blood dominates the absorption in the visible range, while water and lipids dominate in the near infrared range. The graph has on its first, horizontal axis, the wavelength ($\lambda$, lambda) given in nanometers (nm), and on its second, vertical axis, the absorption coefficient $\mu_a$ (mu_a) given in reciprocal centimetres (1/cm).

The total absorption coefficient is a linear combination of the absorption coefficients of for instance blood, water and fat (hence for each component the value of that shown in FIG. 2 multiplied by its volume fraction). By fitting the model to the measurement while using the power law for scattering, the volume fractions of the blood, water and fat as well as the scattering coefficient may be determined. When including other chromophores such as beta-carotene, bile, collagen and elastin, these can be determined in the same way.

Figure 3:
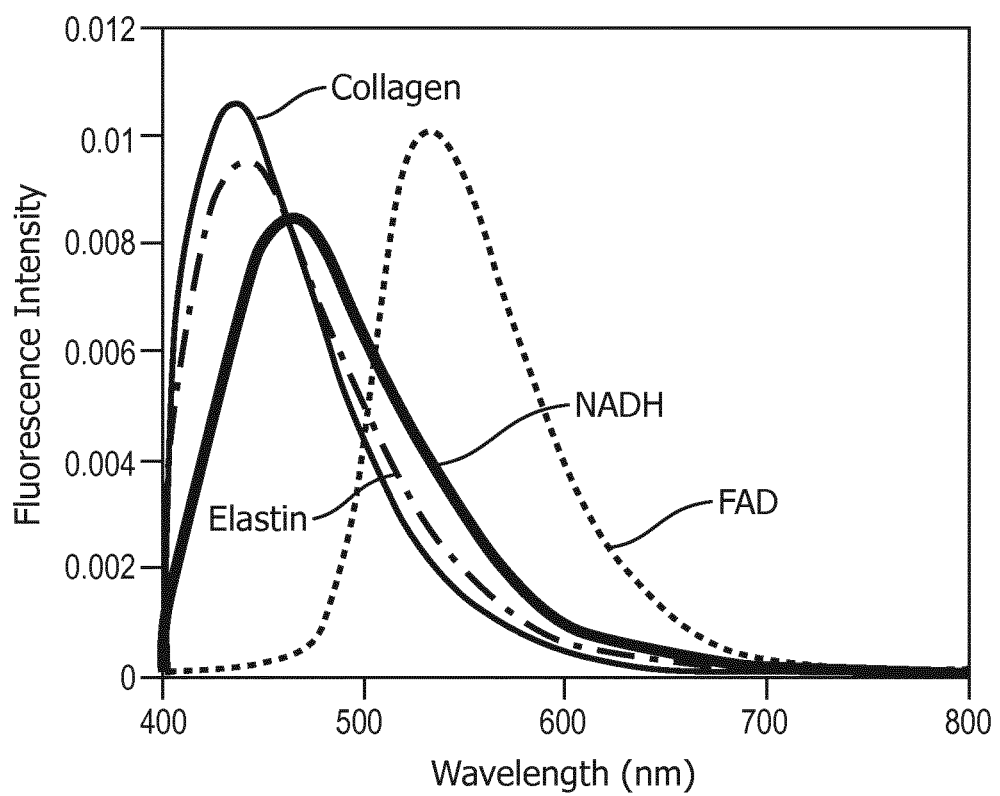
FIG. 3 illustrates the fluorescence intensity of collagen, elastin, NADH and FAD as a function of wavelength.

In addition to diffuse reflectance measurements it is also possible to use the above described diffuse reflectance setup to measure fluorescence spectra. This permits the measurement of parameters such as collagen, elastin, NADH and FAD whose Fluorescence intensity is plotted against wavelength in FIG. 3. The ratio NADH/FAD, termed the optical redox parameter, is of interest as an indicator of the metabolic state of the tissue (see for example M. Müller and B. H. W. Hendriks, "Recovering intrinsic fluorescence by Monte Carlo modelling", J. Biomed. Optics vol. 18 (2013) p. 027009-1 to 027009-13, which can also be used to discriminate tissues.

It is noted that the measurement of data representative of optical spectra of the tissue region 104 can be carried out in various ways in addition to that described in relation to FIG. 1. For example, filter systems in different positions of the optical path may be used; one or more light sources may supply light to or indeed replace source optical fiber 102 in FIG. 1, the light sources being configured to emit in one or more delimited wavelength bands. Furthermore, spectrometers, comprising detectors, for different delimited wavelength bands may be used, or the detectors may have different delimited wavelength bands. This is understood to be commonly known by the skilled person. It is also possible to modulate the various wavelength bands with different modulation frequencies at the source and demodulate these at the detector. This technique is described in the published patent application WO2009/153719 which is hereby incorporated by reference in its entirety. Various other modifications can be envisaged without departing from the scope of the invention; for instance using more than one spectrometer comprising one or more detectors or using more than one light source with different wavelength band, such as Light Emitting Diodes (LEDs) or LASER sources.

Figure 4:
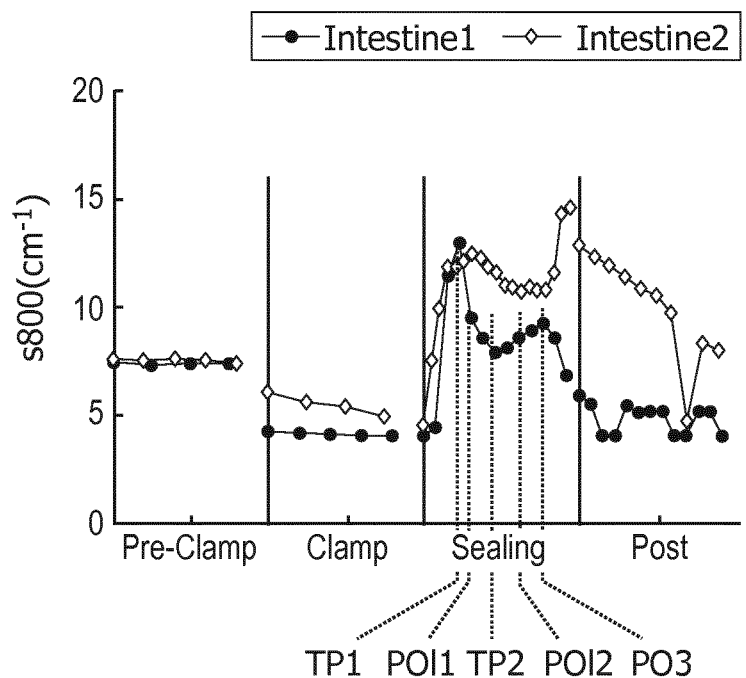
FIG. 4 illustrates the temporal dependence of the optical scattering of tissue during two separate tissue sealing procedures that were performed on an exemplary section of swine intestine.
Figure 5:
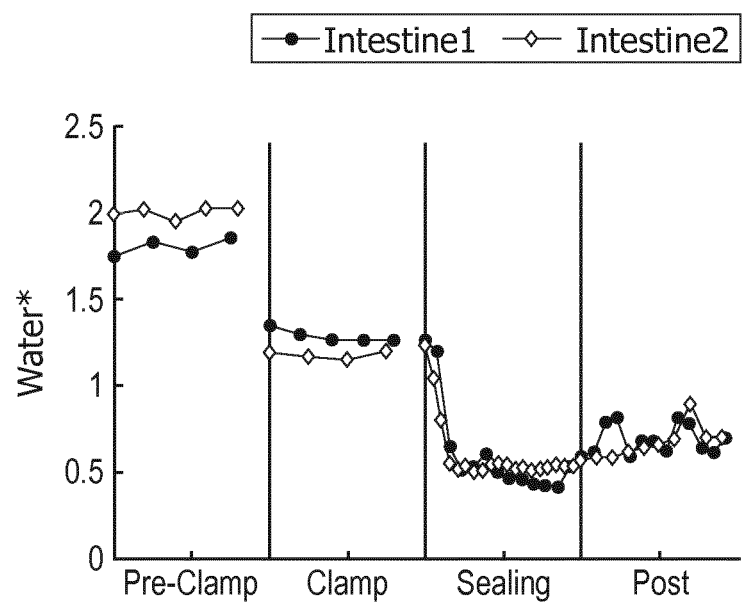
FIG. 5 illustrates the corresponding temporal dependence of the water content of tissue.

FIG. 4 illustrates the temporal dependence of the optical scattering of tissue during two separate tissue sealing procedures that were performed on an exemplary section of swine intestine. FIG. 5 illustrates the corresponding temporal dependence of the water content of tissue. Diffuse optical reflectance spectra were measured using the clamp-type tissue sealing tool of FIG. 1, and the optical scattering, for FIG. 4, and the water content, for FIG. 5, were extracted from the spectra using the above-described diffuse reflectance model. In FIG. 4 and FIG. 5, four stages of a tissue sealing process, are indicated by the horizontal, or time axis. During the pre-clamp phase the jaws of the tissue sealing tool surround the intestine but have not closed onto the tissue. During the clamp phase the jaws of the tissue sealing tool are clamped onto the intestine but no RF energy is applied to the electrodes. During the sealing phase a power is applied to the electrodes, and the power is turned off during the post phase.

Characteristically, during the tissue sealing phase FIG. 4 illustrates an initial rise in the optical scattering until a first turning point TP1, identified for Intestine 1, is reached. Following the first turning point TP1 the scattering passes through a first point of inflection POI1. Tissue sealing is considered to commence at the time of this first point of inflection POI1; thus after the successive occurrence in time of a turning point TP1 and a point of inflection POI1 in the optical scattering signal.

During the time interval immediately prior to the turning point TP1; thus during the time interval between the start of the irradiation of the tissue region with the optical probe beam, or the clamping the tissue sealing device onto tissue, or the time at which the tissue sealing energy of the tissue sealing device is activated, and the time of the turning point TP1; the corresponding water content can be seen in FIG. 5 to reduce. The reduction of water content in the tissue during this period may therefore be seen as confirmation of the onset of tissue sealing. The inventors consider that the first turning point TP1 in the scattering signal is indicative of the generation of steam from the tissue.

Following the time of the first point of inflection POI1 in the scattering signal the corresponding water content does not appear to change significantly during the sealing phase when RF power is applied to the jaws of the tissue sealing tool. Consequently the water content provides little guidance as to when tissue sealing has completed. The optical scattering however does change significantly during the tissue sealing phase. Following the first point of inflection POI1 the optical scattering in FIG. 4 reaches a second turning point TP2. Thus, the successive occurrence in time of a first turning point TP1, a point of inflection POI1, and a second turning point TP2 in the optical scattering may be seen as confirmation of the onset of tissue sealing.

Following the second turning point TP2 the optical scattering in FIG. 4 passes through a second point of inflection POI2. Thus, the successive occurrence in time of a first turning point TP1, a point of inflection POI1, a second turning point TP2 and a second point of inflection POI2 in the optical scattering may be seen as further confirmation of the onset of tissue sealing.

Following the second turning point TP2 the optical scattering in FIG. 4 passes through a third turning point TP3. This turning point TP3 is considered by the inventors to be indicative of the termination of tissue sealing. Consequently the termination of tissue sealing may be indicated by the successive occurrence in time of a second turning point TP2 and a third turning point TP3. The continued application of energy to the sealing tool following the third turning point TP3 is believed to result in tissue damage, ultimately tissue charring. Consequently this point TP3 is indicative of a suitable time to reduce or inhibit the tissue sealing tool's application of energy to the tissue.

Similar, but delayed characteristics are illustrated for Intestine 2 in FIG. 4 and FIG. 5, illustrating the need to tailor the tissue sealing process to the specific tissue that is being sealed in order to avoid delivering too much energy to the tissue, risking burning or charring.

Figure 6:
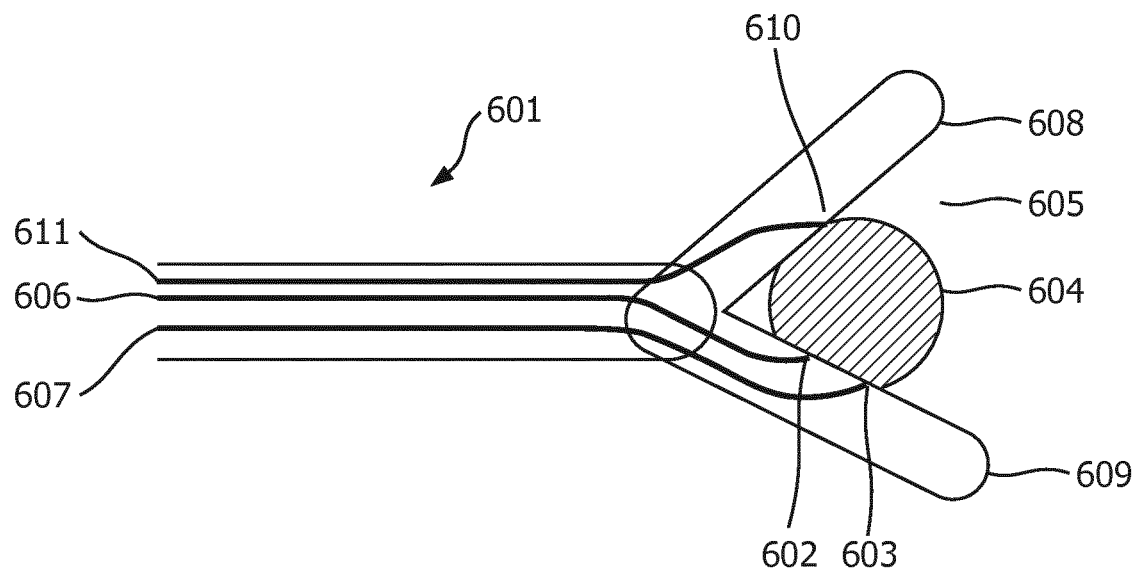
FIG. 6 schematically illustrates another clamp-type tissue sealing tool 601 having optical fibers embedded in its clamp jaws.

FIG. 6 schematically illustrates another clamp-type tissue sealing tool 601 having optical fibers embedded in its clamp jaws. The tissue sealing tool of FIG. 6 may be used to generate optical transmission data corresponding to the different states of tissue sealing in addition to the reflectance, scattering and fluorescence data provided by the optical setup illustrated in FIG. 1. In FIG. 6, source optical fiber 602 is used to irradiate exemplary tissue region 604, such as a portion of a human or animal body, with an optical probe beam; and detector optical fiber 603 receives some of the optical probe beam that has been returned by the tissue region 604 within tissue sealing region 605. A second detector optical fiber 610 receives some of the optical probe beam that has passed through tissue sealing region 605. In addition to the optical measurements acquired by the configuration in FIG. 1, the configuration in FIG. 6 permits measurement of the optical transmission of the tissue sealing region 605. In other words, the tissue sealing tool of FIG. 6 also provides data indicative of the optical probe beam that has passed through the tissue sealing region, or the tissue region. Optical fiber 602 is in communication at its distal end 606 with an optical source, not shown. Optical fibers 603, 610 are in communication at their distal ends 607, 611, with a spectrophotometer, not shown, that includes a beam switching mechanism, not shown, configured to selectively switch between the detection of the portion of the probe beam received by optical fibers 603 or 610 respectively. Consequently the spectrophotometer may selectively perform a measurement of a portion of the probe beam that has been returned by, or passed through tissue sealing region 605 respectively. A broadband halogen optical source generating optical wavelengths from the visible wavelength range to the infrared was used, the source having significant emission approximately in the range 400 nm to 1700 nm. The beam switching mechanism may include a rotatable or deformable mirror, a beamsplitter or the like. Measurements of the optical probe beam that has passed though the tissue sealing region may alternatively be made in the absence of measurements of the optical probe beam that has been returned by the tissue sealing region; thus in some configurations it is contemplated to omit detector optical fiber 603 and the beam switching mechanism altogether.

Figure 7:
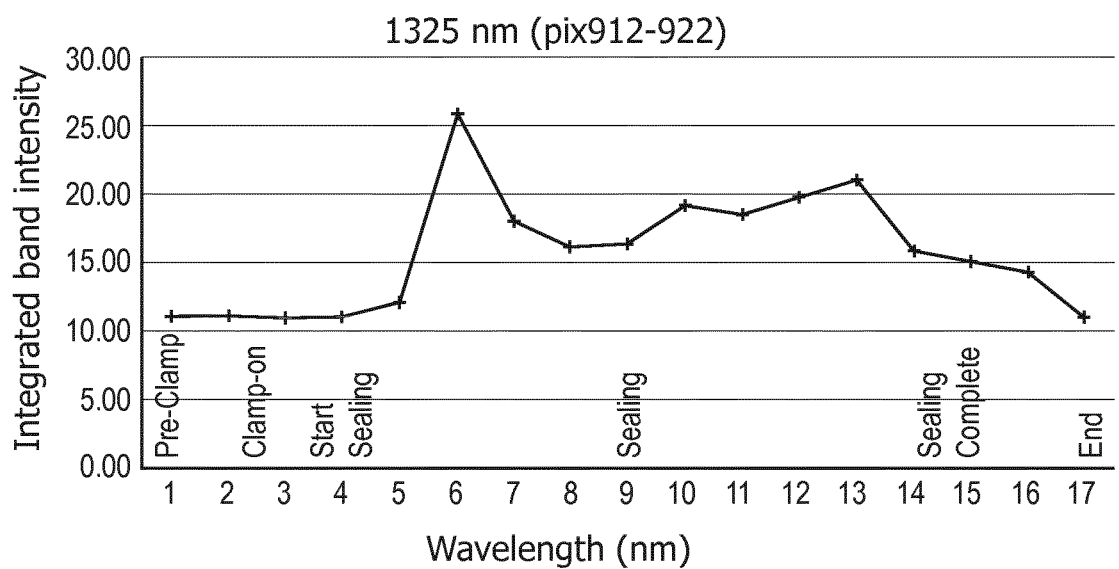
FIG. 7 illustrates the transmission (integrated band intensity, vertical axis) as a function of time (steps 1 to 17 horizontal axis) during the various stages of a tissue sealing process.

The device illustrated in FIG. 6 was used to investigate the optical transmission of an exemplary portion of swine intestine during a tissue sealing procedure. FIG. 7 illustrates the transmission (integrated band intensity, vertical axis) as a function of time (steps 1 to 17 horizontal axis) during the various stages of a tissue sealing process. The graph of FIG. 7 may be correlated with that of FIG. 4 and FIG. 5 in order to improve the accuracy of the indication of a tissue sensing state. At the onset of tissue sealing (step 5) a steep initial rise in transmission is observed, followed by a turning point, and then a fall in the optical transmission and a second turning point. Thus, during the tissue sealing process the optical transmission decreases between a first turning point in the optical transmission and a second turning point in the optical transmission. After the second turning point in the optical transmission the transmission again increases until tissue sealing is complete at step 15. These optical transmission observations are in accordance with a publication by Floume et al titled "Optical, thermal, and electrical monitoring of radio-frequency tissue modification", J. Biomedical Optics 15 (2010) p 018003-1. Thus, optical transmission measurements of at least a portion of the optical probe beam that has passed through the tissue sealing region may be used to further improve the indication of either the onset or the termination of tissue sealing. These optical transmission measurements may for example be correlated with any combination of the previously described changes in optical scattering, such as the time of the first turning point TP1, the time of the first point of inflection POI1, the time of the second turning point TP2, the time of the second point of inflection POI2 to further improve the indication of either the onset or the termination of tissue sealing.

Other optical parameters may be extracted from the measured optical spectra and used to supplement the above described changes in optical scattering in order to further improve the accuracy of the indication of the onset of tissue sealing, or the termination of tissue sealing. Optical parameters indicative of collagen, lipid, oxyhaemoglobin, de-oxyhaemoglobin, or methaemoglobin content in the tissue region may also be determined by applying the above described diffusion theory model to optical spectra acquired using the above described diffuse reflectance spectroscopy setup, or to spectra acquired in an optical transmission or fluorescence detection configuration.

The above indications of the onset of tissue sealing, and the termination of tissue sealing, may be used in a tissue sealing device or a tissue cutting device to indicate when a particular tissue sealing state has been reached. One or more of these states may furthermore be used by the tissue sealing or tissue cutting tool to control its tissue sealing or tissue cutting power or energy. By providing feedback to the device in this way an improved tissue seal may be achieved because the energy or power can be tailored to the specific type of tissue undergoing the sealing process. By preventing the delivery of too much power or energy to the tissue, the device can provide an optimal seal since undesirable phases such as tissue charring can be avoided.

In one embodiment an energy-based tissue sealing or tissue cutting device has a tissue sealing zone; the tissue sealing device comprising: an energy delivery unit for delivering energy to a tissue region within the tissue sealing zone; an optical source configured to irradiate at least a portion of the tissue sealing zone with an optical probe beam; at least one optical detector configured to receive at least a portion of the optical probe beam that has passed through or been returned from within the tissue sealing zone; and an optical analysis unit configured to: generate a signal indicative of optical scattering in the tissue sealing zone from the received optical probe beam; and to indicate an onset of tissue sealing based on the successive occurrence in time of a turning point and a point of inflection in the optical scattering signal. The energy-based tissue sealing device may for example be an electro-surgical tissue sealing device, such as an electro-surgical tissue welding device; and the energy-based tissue cutting device may for example be an electro-surgical cutting device, such as an electro-surgical knife. The optical analysis unit may for example include a processor. The energy delivery unit may for example be an RF power source, a thermal power source or an optical power source.

In another embodiment the energy-based tissue sealing device further comprises an energy regulation unit in operative communication with the energy delivery unit; wherein the energy regulation unit is configured to control the energy delivered by the energy delivery unit based on the onset of tissue sealing. The power may be either reduced in this phase to effect a longer sealing period, or increased in order to rapidly seal the tissue. In another embodiment the energy regulation unit may be configured to change the energy or power of the tissue sealing device subsequent in time to the first turning point TP1 in the optical scattering signal. The energy or power may be increased or decreased at this point and is desirably decreased.

In another embodiment the energy regulation unit may be configured to change the energy or power of the tissue sealing device after the successive occurrence in time of the first turning point TP1 and the second turning point TP2 in the optical scattering signal. Desirably the energy or power should be increased in order to effect a more rapid tissue seal.

In another embodiment the energy regulation unit may be configured to decrease the energy or power of the tissue sealing device following the successive occurrence in time of the second turning point TP2 in the optical scattering signal and the third turning point TP3 of the optical scattering signal. Desirably the energy or power should be decreased since these events are indicative of a termination of the tissue sealing process. Preferably the energy or power should be switched off at this stage.

The present invention is described below by means of a number of examples.

1st Example. Method of determining a state of tissue sealing, the method comprising the steps of:
    irradiating a tissue region with an optical probe beam;
    receiving at least a portion of the optical probe beam that has passed through or been returned by the tissue region;
    generating a signal indicative of optical scattering in the tissue region from the received optical probe beam;
    indicating an onset of tissue sealing based on the successive occurrence in time of a turning point (TP1) and a point of inflection (POI1) in the optical scattering signal.

2nd Example. Method of Example 1 wherein the onset of tissue sealing is indicated based further on a second turning point (TP2) in the optical scattering signal, wherein the second turning point (TP2) in the optical scattering signal succeeds the point of inflection (POI1).

3rd Example. Method of Example 2 wherein the onset of tissue sealing is indicated based further on a second point of inflection (POI2) in the optical scattering signal, wherein the second point of inflection (POI2) in the optical scattering signal succeeds the second turning point (TP2).

4th Example. Method of Example 2 further comprising the step of indicating a termination of tissue sealing; wherein the termination of tissue sealing is indicated based on a third turning point (TP3) in the optical scattering signal, wherein the third turning point (TP3) in the optical scattering signal succeeds the second turning point (TP2).

5th Example. Method according to any one of Examples 1-4 further comprising the step of generating a signal indicative of water content in the tissue region from the received optical probe beam;
wherein the onset of tissue sealing is indicated based further on a reduction of water content in the tissue immediately prior to the turning point (TP1).

6th Example. Method according to any one of Examples 1-4 further comprising the step of generating a signal indicative of at least one of: water, collagen, lipid, elastin, β-carotene, lycopene, α-carotene, oxyhaemoglobin, de-oxyhaemoglobin, methaemoglobin, or exogenous dye content in the tissue region from the received optical probe beam;
wherein either the onset of tissue sealing, or the termination of tissue sealing is indicated based further on at least one of said parameters traversing a predetermined threshold.

7th Example. Method of controlling a tissue sealing power of a thermal or optical tissue sealing device comprising the steps of:
    determining an onset of tissue sealing by performing the method of any one of Examples 1-6; and
    changing the tissue sealing power based on the indicated onset of tissue sealing.

8th Example. Method of Example 7 wherein the tissue sealing power is changed subsequent in time to the turning point (TP1) in the optical scattering signal.

9th Example. Method of Example 8 wherein the tissue sealing power is changed after the successive occurrence in time of the turning point (TP1) and the second turning point (TP2) in the optical scattering signal.

10th Example. Method of Example 9 wherein the tissue sealing power is decreased following the successive occurrence in time of the second turning point (TP2) in the optical scattering signal and the third turning point (TP3) of the optical scattering signal.

11th Example. Method according to any one of Examples 1-10 wherein the step of generating a signal indicative of optical scattering in the tissue region from the received optical probe beam includes the steps of:
    measuring at least a portion of the optical spectrum of the received optical probe beam; and
    applying a diffusion reflectance model to the optical spectrum of the received optical probe beam.

12th Example. Method according to any one of Example 5 or 6 wherein the either step of generating a signal indicative of water content in the tissue region from the received optical probe beam, or the step of generating a signal indicative of at least one of: collagen, lipid, elastin, β-carotene, lycopene, α-carotene, oxyhaemoglobin, de-oxyhaemoglobin, methaemoglobin, or exogenous dye content in the tissue region from the received optical probe beam; is generated by the steps of:
    applying a diffuse reflectance model to the optical spectrum of the received optical probe beam; and
    separating a scattering component of the optical spectrum from an absorption spectrum of at least one of: water, collagen, lipid, elastin, β-carotene, lycopene, α-carotene, oxyhaemoglobin, de-oxyhaemoglobin, methaemoglobin, or exogenous dye content in the optical spectrum.

13th Example. Computer program product comprising instructions which when carried out on a computer cause the computer to perform the method of any one of Examples 1-12.

14th Example. Energy-based tissue sealing or tissue cutting device (101, 601) having a tissue sealing zone (105, 605); the device comprising:
    an energy delivery unit (108, 109, 608, 609) for delivering energy to a tissue region (104, 604) within the tissue sealing zone (105, 605);
    an optical source (102, 602) configured to irradiate at least a portion of the tissue sealing zone with an optical probe beam;
    at least one optical detector (103, 603, 610) configured to receive at least a portion of the optical probe beam that has passed through or been returned from within the tissue sealing zone; and
    an optical analysis unit configured to:
        generate a signal indicative of optical scattering in the tissue sealing zone from the received optical probe beam; and to
        indicate an onset of tissue sealing based on the successive occurrence in time of a turning point (TP1) and a point of inflection (POI1) in the optical scattering signal.

15th Example. Energy-based tissue sealing or tissue-cutting device according to Example 14 further comprising an energy regulation unit in operative communication with the energy delivery unit;
wherein the energy regulation unit is configured to control the energy delivered by the energy delivery unit based on the onset of tissue sealing.

To summarize, a method for determining a state of tissue sealing is disclosed wherein an optical probe beam is used to irradiate a tissue region. A signal indicative of optical scattering in the tissue region is generated from part of the optical probe beam that has passed through or been returned by the tissue region. The onset of tissue sealing is indicated by the successive occurrence in time of a turning point and a point of inflection in the optical scattering signal. An energy-based tissue sealing or tissue-cutting device for use in accordance with the method is also disclosed.

Whilst the invention has been illustrated and described in detail in the drawings and foregoing description, such illustrations and description are to be considered illustrative or exemplary and not restrictive; the invention is not limited to the disclosed embodiments and can be used for determining a tissue sealing state in surgical probes in general.

The invention claimed is:

1. An energy based tissue sealing or tissue cutting device having a tissue sealing zone, the tissue cutting device comprising:
   an energy delivery unit for delivering energy to a tissue region within the tissue sealing zone;
   an optical source configured to irradiate at least a portion of the tissue sealing zone with an optical probe beam;
   at least one optical detector configured to receive at least a portion of the optical probe beam that has passed through or been returned from within the tissue sealing zone; and
   an optical analysis unit configured to:
   generate an optical scattering coefficient indicative of optical scattering in the tissue sealing zone from the received at least portion of the optical probe beam; and
   indicate an onset of tissue sealing based on a successive occurrence in time of a turning point and a point of inflection in the optical scattering coefficient.

2. The energy based tissue sealing or tissue cutting device of claim 1, wherein the onset of tissue sealing is indicated based further on a second turning point in the optical scattering coefficient, wherein the second turning point in the optical scattering coefficient succeeds the point of inflection.

3. The energy based tissue sealing or tissue cutting device of claim 2, wherein: the optical analysis unit is further configured to indicate a termination of tissue sealing; the termination of tissue sealing is indicated based on a third turning point in the optical scattering coefficient; and the third turning point in the optical scattering coefficient succeeds the second turning point.

4. The energy based tissue sealing or tissue cutting device of claim 1, wherein the onset of tissue sealing is indicated based further on a second point of inflection in the optical scattering coefficient, wherein the second point of inflection in the optical scattering coefficient succeeds the second turning point (TP2).

5. The energy based tissue sealing or tissue cutting device of claim 1, wherein: the optical analysis unit is further configured to generate a signal indicative of water content in the tissue region from the received at least portion of the optical probe beam:
   and the onset of tissue sealing is indicated based further on a reduction of water content in the tissue immediately prior to the turning point.

6. The energy based tissue sealing or tissue cutting device of claim 1, wherein: the optical analysis unit is further configured to generate a signal indicative of at least one of: water, collagen, lipid, elastin, β-carotene, lycopene, α-carotene, oxyhaemoglobin, de-oxyhaemoglobin, methaemoglobin, or exogenous dye content in the tissue region from the received at least portion of the optical probe beam; and either the onset of tissue scaling, or the termination of tissue sealing is indicated based further on at least one of said parameters traversing a predetermined threshold.

7. The energy based tissue sealing or tissue cutting device of claim 6, wherein the optical analysis unit is configured to generate the optical scattering coefficient indicative of optical scattering in the tissue sealing zone by:
   measuring at least a portion of the optical spectrum of the received at least portion of the optical probe beam; and
   extracting the optical scattering coefficient from the at least a portion of the measured optical spectrum of the received at least portion of the optical probe beam.

8. The energy based tissue sealing or tissue cutting device of claim 6, wherein the optical analysis unit is configured to generate the optical scattering coefficient indicative of optical scattering in the tissue sealing zone by:
   measuring at least a portion of the optical spectrum of the received at least portion of the optical probe beam; and
   applying a diffuse reflectance model to the optical spectrum of the received at least portion of the optical probe beam.

9. The energy based tissue sealing or tissue-cutting device according to claim 8, further comprising an energy regulation unit in operative communication with the energy delivery unit, wherein the energy regulation unit is configured to control the energy delivered by the energy delivery unit based on the onset of tissue scaling.

10. A non-transitory tangible computer-readable storage medium comprising instructions which when carried out on a computer cause the computer to perform a method of determining a state of tissue sealing, the method comprising:
    irradiating a tissue region with an optical probe beam;
    receiving at least a portion of the optical probe beam that has passed through or been returned by the tissue region;
    generating an optical scattering coefficient indicative of optical scattering in the tissue region from the received at least portion of the optical probe beam; and
    indicating an onset of tissue sealing based on a successive occurrence in time of a turning point and a point of inflection in the optical scattering coefficient.

11. The non-transitory tangible computer-readable storage medium of claim 10, wherein: the onset of tissue sealing is indicated based further on a second turning point in the optical scattering coefficient; and the second turning point in the optical scattering coefficient succeeds the point of inflection.

12. The non-transitory tangible computer-readable storage medium of claim 11, further comprising indicating a termination of tissue sealing, wherein: the termination of tissue sealing is indicated based on a third turning point in the optical scattering coefficient; and wherein the third turning point in the optical scattering coefficient succeeds the second turning point.

13. The non-transitory tangible computer-readable storage medium according to claim 10, further comprising controlling a tissue sealing power of a thermal or optical tissue sealing device based on the indicated onset of tissue sealing.

14. The non-transitory tangible computer-readable storage medium according to claim 10, wherein the generating the optical scattering coefficient indicative of optical scattering in the tissue region from the received at least portion of the optical probe beam further comprises:
    measuring at least a portion of the optical spectrum of the received at least portion of the optical probe beam; and
    extracting the optical scattering coefficient from the at least a portion of the measured optical spectrum of the received at least portion of the optical probe beam.

15. The non-transitory tangible computer-readable storage medium according to claim 10, wherein the generating the optical scattering coefficient indicative of optical scattering in the tissue region from the received at least portion of the optical probe beam further comprises:

measuring at least a portion of the optical spectrum of the received at least portion of the optical probe beam; and applying a diffuse reflectance model to the optical spectrum of the received at least portion of the optical probe beam.

16. A method of determining a state of tissue sealing, the method comprising:

irradiating a tissue region with an optical probe beam;

receiving at least a portion of the optical probe beam that has passed through or been returned by the tissue region;

generating an optical scattering coefficient indicative of optical scattering in the tissue region from the received at least portion of the optical probe beam; and indicating an onset of tissue sealing based on a successive occurrence in time of a turning point and a point of inflection in the optical scattering coefficient.

17. The method of claim 16, wherein the onset of tissue sealing is indicated based further on a second turning point in the optical scattering coefficient, wherein the second turning point in the optical scattering coefficient succeeds the point of inflection.

18. The method of claim 17, further comprising indicating a termination of tissue sealing, wherein: the termination of tissue sealing is indicated based on a third turning point in the optical scattering coefficient; and the third turning point in the optical scattering coefficient succeeds the second turning point.

19. The method according to claim 16, further comprising controlling a tissue sealing power of a thermal or optical tissue sealing device based on the indicated onset of tissue sealing.

20. The method of claim 16, wherein the generating the optical scattering coefficient indicative of optical scattering in the tissue region from the received at least portion of the optical probe beam further comprises:

measuring at least a portion of the optical spectrum of the received at least portion of the optical probe beam; and extracting the optical scattering coefficient from the at least a portion of the measured optical spectrum of the received at least portion of the optical probe beam.

* * * * *